United States Patent
Schmid-Schoenbein et al.

(10) Patent No.: US 6,592,746 B1
(45) Date of Patent: Jul. 15, 2003

(54) SENSOR PROBE FOR DETERMINING HYDROGEN PEROXIDE CONCENTRATION AND METHOD OF USE THEREOF

(75) Inventors: Geert W. Schmid-Schoenbein, Del Mar, CA (US); Dale A. Baker, San Diego, CA (US); David Gough, Cardiff, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/673,223
(22) PCT Filed: Apr. 12, 1999
(86) PCT No.: PCT/US99/07991
  § 371 (c)(1),
  (2), (4) Date: Oct. 13, 2000
(87) PCT Pub. No.: WO99/53301
  PCT Pub. Date: Oct. 21, 1999

Related U.S. Application Data
(60) Provisional application No. 60/081,591, filed on Apr. 14, 1998.

(51) Int. Cl.[7] ..................... G01N 27/327; G01N 27/404
(52) U.S. Cl. ................. 205/778; 204/403.01; 204/415; 205/783
(58) Field of Search .................... 204/415, 403.01; 205/782, 782.5, 783, 777.5, 778

(56) References Cited

U.S. PATENT DOCUMENTS

| | | | |
|---|---|---|---|
| 3,539,455 A | * | 11/1970 | Clark |
| 3,542,662 A | * | 11/1970 | Hicks et al. |
| 3,707,455 A | * | 12/1972 | Derr et al. |
| 3,979,274 A | * | 9/1976 | Newman |

(List continued on next page.)

FOREIGN PATENT DOCUMENTS

| | | | |
|---|---|---|---|
| JP | 02057958 | * | 2/1990 |
| WO | WO90/02202 | | 8/1990 |
| WO | WO94/02629 | | 3/1994 |

OTHER PUBLICATIONS

Stein, "Catalase Biosensor for the Determination of Hydrogen, Fluroide and Cyanide", Mikrochim. Acta (1995)month unavailable, 118(1–2), 93–101, XP002110265.*

(List continued on next page.)

*Primary Examiner*—T. Tung
(74) *Attorney, Agent, or Firm*—Brown Martin Haller & McClain LLP

(57) ABSTRACT

A sensor probe is disclosed which can measure the hydrogen peroxide content of a single sample using two oxygen sensors whose electrodes are encased in defined membranes. The oxygen reference sensor is encased in a hydrophobic membrane which prevents the transport of hydrogen peroxide or electrochemical poisons or interferents and isolates the electrodes and an electrolyte fluid surrounding the electrodes from the sample fluid. The hydrogen-peroxide-generated oxygen (HPGO) sensor is also is encased in such a hydrophobic membrane, but has in series with and distally of the hydrophobic membrane a hydrophilic membrane which contains an immobilized enzyme such as catalase, peroxidase or other enzymes of a family which catalyzes the reaction of hydrogen peroxide to oxygen and water. At the HPGO sensor, the hydrogen peroxide is catalyzed to oxygen by the enzyme so that the HPGO sensor measures an enhanced concentration of oxygen relative to the oxygen reference sensor. The signals of each of the oxygen sensors are sent to a summer, which subtracts the equal background oxygen concentration of both, yielding a resultant difference signal representative of the concentration of hydrogen peroxide content of the sample itself. A suitable display or data collection device is used to capture the information in visible or digital form. Methods of use of the device for determining hydrogen peroxide content of human or animal tissues or fluids, or environmental or industrial fluids or fluid-containing materials, are also disclosed.

34 Claims, 1 Drawing Sheet

U.S. PATENT DOCUMENTS

| | | | | |
|---|---|---|---|---|
| 4,340,448 A | * | 7/1982 | Shiller et al. |
| 4,671,288 A | * | 6/1987 | Gough |
| 4,721,677 A | * | 1/1988 | Clark |
| 5,320,725 A | | 6/1994 | Gregg |
| 5,352,348 A | * | 10/1994 | Young et al. |

OTHER PUBLICATIONS

Posch et al, "Optical Sensor for Hydrogen Peroxide", Mikrochim. Acta (1989)month unavailable, 1(1–2), 41–50, XP002110266.*

F. Lacy, D.A. Gough and G.W. Schmid–Schoenbein, "Role of xanthine oxidase in hydrogen peroxide production." *Free Radical Biology & Medicine*. 25:720–7.

F. Lacy, D.T. O'Connor and G.W. Schmid–Schoenbein, "Plasma hydrogen peroxide production in hypertensives and normotensive subjects at genetic risk for hypertension." *J. Hypertension*. 16:291–303.

A.S. Swei, F. Lacy, F.A. Delano and G.W. Schmid–Schoenbein, "Oxidative stress in the Dahl hypertensive rat" *Hypertension* 30:1628–33.

A.P.F. Turner, "Biosensors: Past, present and future." *Essays in Biotechnology*, c.. 1996. http://www.cranfield.ac.uk/biotech/chinap.htm.

"HPLC Electrochemical detection: The working electrode." (published before Aug. 24, 1998) http://www.esainc.com/esatech/esaworkeletro.html.

* cited by examiner

SENSOR PROBE FOR DETERMINING HYDROGEN PEROXIDE CONCENTRATION AND METHOD OF USE THEREOF

RELATED APPLICATIONS

This application claims the benefit of priority under 35 U.S.C. §119(e) of U.S. provisional application Ser. No. 60/081,591 to Geert W. Schmid-Schoenbein, Dale Baker and David Gough, filed Apr. 14, 1998, and also claims the benefit of priority under 35 U.S.C. §371 of PCT application Ser. No. PCT/US99/07991, filed Apr. 12, 1999, the subject matter of which is incorporated herein by reference.

FIELD OF THE INVENTION

The present invention relates to a hydrogen peroxide sensor for fluids, and applications therefore. In particular, the present invention relates to a sensor which permits continuous monitoring of hydrogen peroxide in fluids and use of the data from the sensor for various purposes, including predicting hypertension and other oxidative stress-related physical conditions.

BACKGROUND OF THE INVENTION

Hydrogen peroxide is formed in several biological and environmental processes. Hydrogen peroxide can be found in natural water (e.g., sea water, rain water), where it is an important species in redox reactions, in industrial processes, including drinking water purification, where it is used as a disinfectant, and in biological tissues, including blood, as a result of enzymatic reactions. Direct detection of hydrogen peroxide is an important analytical task, and numerous techniques have been devised for measurement of hydrogen peroxide levels in fluids as indications of, for example, medical conditions, environmental quality, or the presence of pathogens in cells of both animals and plants. Superoxide radicals ($O_2^-$) in living tissue can be derived from many sources, such as activated granulocytes, endothelial cells, xanthine oxidase-catalyzed reactions, mitochondrial metabolism, and transition metal reactions with oxygen. Hydrogen peroxide ($H_2O_2$) can be produced from the dismutation of superoxide radicals catalyzed by the enzyme superoxide dimutase (SOD), from transition metal reactions with superoxide radicals, and from enzymes (e.g., glycollate oxidase and urate oxidase) which produce peroxide directly without first producing superoxide. The presence of antioxidants, including certain enzymes such as SOD and catalase, serves to limit the concentration of the reactive oxygen species in plasma and tissues. Therefore, either an increase in the production of free radicals and/or a decrease in antioxidants can cause oxidative stress, contributing to possible cardiovascular complications in animals. Similarly, oxygen free radicals may affect vascular resistance by inactivating nitric oxide (NO), thereby causing arteriolar vasoconstriction and elevation of peripheral hemodynamic resistance. Other conditions have also been associated with oxidative stress, including arthritis, acceleration of the progression of HIV to full-blown AIDS, and neurological diseases such as ALS.

The mortality of individuals with hypertension has been found to be more than double that of the normotensive population, with most of the deaths occurring suddenly. Untreated hypertension also predisposes individuals to end organ damage or failure, including cerebrovascular accident (e.g., intracranial hemorrhage, encephalopathy), myocardial infarction, renal failure, and retinal hemorrhage. The mechanisms that predispose individuals with elevated arterial pressure to develop vascular organ injury are only partially understood. Oxygen free radicals and related intermediates have been implicated in hypertension and may play a role by affecting vascular smooth muscle contraction and resistance to blood flow. In individuals with histories of conditions such as atherosclerosis, stroke and myocardial infarction, hypertension constitutes a risk factor.

Studies have shown that in persons with essential hypertension there exists not only reduced antioxidant enzyme and nitric oxide levels, but also an increase in the NADPH oxidase activity on neutrophil membranes. An increase in NADPH oxidase activity results in production of oxygen free radicals. Consequently, hypertensives (individuals experiencing increased systolic and diastolic blood pressures) have higher superoxide and hydrogen peroxide production by neutrophils than normotensive (individuals with normal blood pressure) controls. It has also been shown that hypertensive patients revert to normal free radical, antioxidant and nitric oxide levels after effective antihypertensive treatment.

A number of different techniques are known for measurement of oxygen free radicals and their intermediates. These methods include the use of electrodes, chemiluminescence, and fluorescence. All of the aforementioned methods are limited to measuring oxygen free radicals from stimulated neutrophils or deproteinized whole blood.

A new hydrogen peroxide sensing system for measuring hydrogen peroxide in plasma is disclosed in international PCT patent application PCT/US 98/19013 (filed Sep. 14, 1998). In this system the test sample of plasma from a fluid or fluid-containing material which is to be analyzed for hydrogen peroxide content is divided into two equal portions and a hydrogen peroxide oxidation sensor is inserted into each portion. An inhibitor for the enzyme catalase, such as sodium azide, is added to one of the portions to stabilize the hydrogen peroxide present. A quantity of catalase is added to the other portion to deplete any hydrogen peroxide present by catalyzing it to oxygen. Hydrogen peroxide oxidation of each portion at the respective sensor is then measured, along with background oxidation of any other oxidizable species in the sample. The signal from the sensor in the depleted hydrogen peroxide sample is subtracted from the signal from the stabilized hydrogen peroxide sample to eliminate the signals' contributions from background oxidation, thus yielding a resultant signal which is representative of the amount of hydrogen peroxide production in the subject fluid or material.

While the system described in that PCT application is quite useful, it requires two separate portions of the plasma from the sample fluid or material as well as chemical treatment of each of the portions. Such a system is useful primarily in a laboratory where there are facilities for chemically treating the portions, and where supplies of the treating chemicals can be made available. It is not, however, particularly useful for analysis of samples in the field or where the treating chemicals are not conveniently available. It also does not account for the fact that either or both of the treating agents may affect other components of the samples so that the two samples may end up being different from each other with respect to more than just the hydrogen peroxide component. Further, since the treating chemicals or enzymes must be added to each sample, the device must be recalibrated for each run.

SUMMARY OF THE INVENTION

We have now developed a new sensor probe which can measure hydrogen peroxide content of a single sample of a fluid or fluid-containing material (such as blood, tissue, environmental water steams or industrial water streams) using two oxygen sensors whose electrodes are encased in specified membranes. Each sensor has an oxygen sensing electrode group and both groups are inserted into the single sample of fluid or fluid-containing material, so that both measure from a homogeneous source, preventing testing errors due to differential reactions with treating chemicals.

The electrode end of each sensor is surrounded by a hydrophobic membrane which prevents the transport of electrochemical poisons or interferents and isolates the electrodes and an electrolyte fluid surrounding the electrodes from the sample fluid. The hydrophobic membrane is permeable to oxygen but not to hydrogen peroxide. The hydrogen-peroxide-generated-oxygen (HPGO) sensor also is encased in a hydrophilic membrane which contains an enzyme such as catalase, peroxidase or other enzymes of a family which catalyzes the reaction of hydrogen peroxide to oxygen and water, namely:

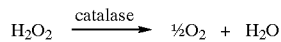

$$H_2O_2 \xrightarrow{catalase} \tfrac{1}{2}O_2 + H_2O$$

This hydrophilic membrane is permeable to both hydrogen peroxide and oxygen. It is positioned in series with the hydrophobic membrane, with the hydrophobic membrane disposed between the hydrophilic membrane and the electrodes of the first sensor.

Disposed within the contained volume or space formed by the inner (proximal) surface of each hydrophobic membrane and the electrodes of its respective sensor, is an electrolyte solution to provide for migration of oxygen or electric charge to the appropriate electrodes. The electrolyte will be a fluid which is chemically inert to oxygen.

In operation the concentration gradient of oxygen in the test sample causes its diffusion across the membrane or membranes surrounding each sensor. The hydrophobic, pore free membranes surrounding each sensor prevent the diffusion of hydrogen peroxide and electrolytic poisons or interferents. At the oxygen reference sensor which is encased by only the hydrophobic membrane, only sample (background) oxygen diffuses into the internal electrolyte fluid until its concentrations in the electrolyte and test sample are equal. At the HPGO sensor, however, the hydrogen peroxide encounters the hydrophilic membrane with its catalase content. Catalytic reaction of the hydrogen peroxide with the catalase within the membrane results in the generation of oxygen in excess over the background sample oxygen level and the depletion of the hydrogen peroxide, so that the total quantity of oxygen which diffuses toward the HPGO sensor out of the hydrophilic membrane and through the hydrophobic membrane comprises both the background sample oxygen and the oxygen reaction product from the catalase-catalyzed conversion of the hydrogen peroxide.

The oxygen content is each fluid electrolyte is then detected by the respective sensors and the signals of each of the oxygen sensors are sent to a summer, which cancels out (subtracts) the portion of each signal due to the equal background oxygen concentration seen by each sensor. The resultant difference signal output by the summer thus represents only the quantity of oxygen generated by the conversion of the hydrogen peroxide at the HPGO sensor, and thus is a measure of the hydrogen peroxide content of the sample itself. A suitable display or data collection device may receive the resultant signal and provide a visible readout representing the hydrogen peroxide content, or the device may collect the signal data in electronic form which can be subsequently stored, manipulated and recovered.

Thus, in a broad embodiment, the invention is of a sensing probe for quantitative determination of hydrogen peroxide present in a body of fluid or fluid-containing material, which comprises first and second oxygen sensors, each generating a signal proportional to oxygen content of a fluid electrolyte in contact with a respective sensor; first and second membranes disposed in series and separating the first oxygen sensor from the material, with the second membrane being disposed between the first membrane and the first oxygen sensor; a third membrane separating the second oxygen sensor from the material; the first membrane being permeable to hydrogen peroxide and oxygen, and having dispersed therethrough an immobilized enzyme which catalyzes the conversion of hydrogen peroxide to oxygen; the second and third membranes being hydrophobic and permeable to oxygen but not hydrogen peroxide; and a summer receiving oxygen-content-dependent signals from the first and second oxygen sensors and generating a resultant signal proportional to the difference between the oxygen-content-dependent signals, the difference being proportional to the concentration of hydrogen peroxide in the sample.

In another broad embodiment the invention is of a sensing probe for quantitative determination of hydrogen peroxide present in a body of fluid or fluid-containing material, which comprises a first oxygen sensor and a second oxygen sensor, each having electrode means for detecting the presence of oxygen in a fluid electrolyte in contact with the electrode means and for generating a signal proportional to the concentration of oxygen detected in the fluid electrolyte; a first membrane surrounding the electrode means of the first oxygen sensor, forming a barrier between the electrode means and the material and being permeable to oxygen and hydrogen peroxide, the first membrane having disposed therethrough an immobilized enzyme which catalyzes conversion of hydrogen peroxide to oxygen; a second membrane and a third membrane, the second membrane also surrounding the electrode means of the first sensor in series with the first membrane and being disposed between the first membrane and the electrode means, and the third membrane surrounding the electrode means of the second sensor and forming a barrier between the electrode means of the second sensor and the material, the second and third membranes being hydrophobic and permeable to oxygen but not hydrogen peroxide; a summer electrically connected to the first and second oxygen sensors and receiving a signals from each sensor proportional to the amount of oxygen detected by the electrode means of the sensor, the summer comprising comparison means for determining difference in value between a signal from the first oxygen sensor and a signal from the second oxygen sensor and transmitting a difference signal proportional to the difference in value to a receiver; and the receiver comprising conversion means for receiving the difference signal and converting it into a human- or machine-readable indication of the concentration of hydrogen peroxide in the material.

Also a part of the present invention is a method of making a quantitative determination of hydrogen peroxide present in a body of fluid or fluid-containing material, such as human or animal tissue or bodily fluid or an environmental or industrial fluid or fluid-containing material, which comprises placing the fluid or fluid containing material in operative contact with a sensor probe of this invention, and operating the sensor probe to generate the human- or machine-readable indication of concentration of the hydrogen peroxide in the material.

The sensor probe thus provides for simple and rapid determination of the hydrogen peroxide content of a sample of tissue, blood, other bodily fluid or environmental or industrial fluid at any convenient facility and without the necessity of having additional chemicals present. The probe can advantageously be used in hospital settings, intensive care units, rehabilitation units, field locations, industrial plants or other locations where assays of hydrogen peroxide may be necessary or helpful.

BRIEF DESCRIPTION OF THE DRAWING

The single

DETAILED DESCRIPTION AND PREFERRED EMBODIMENT

Figure 1:
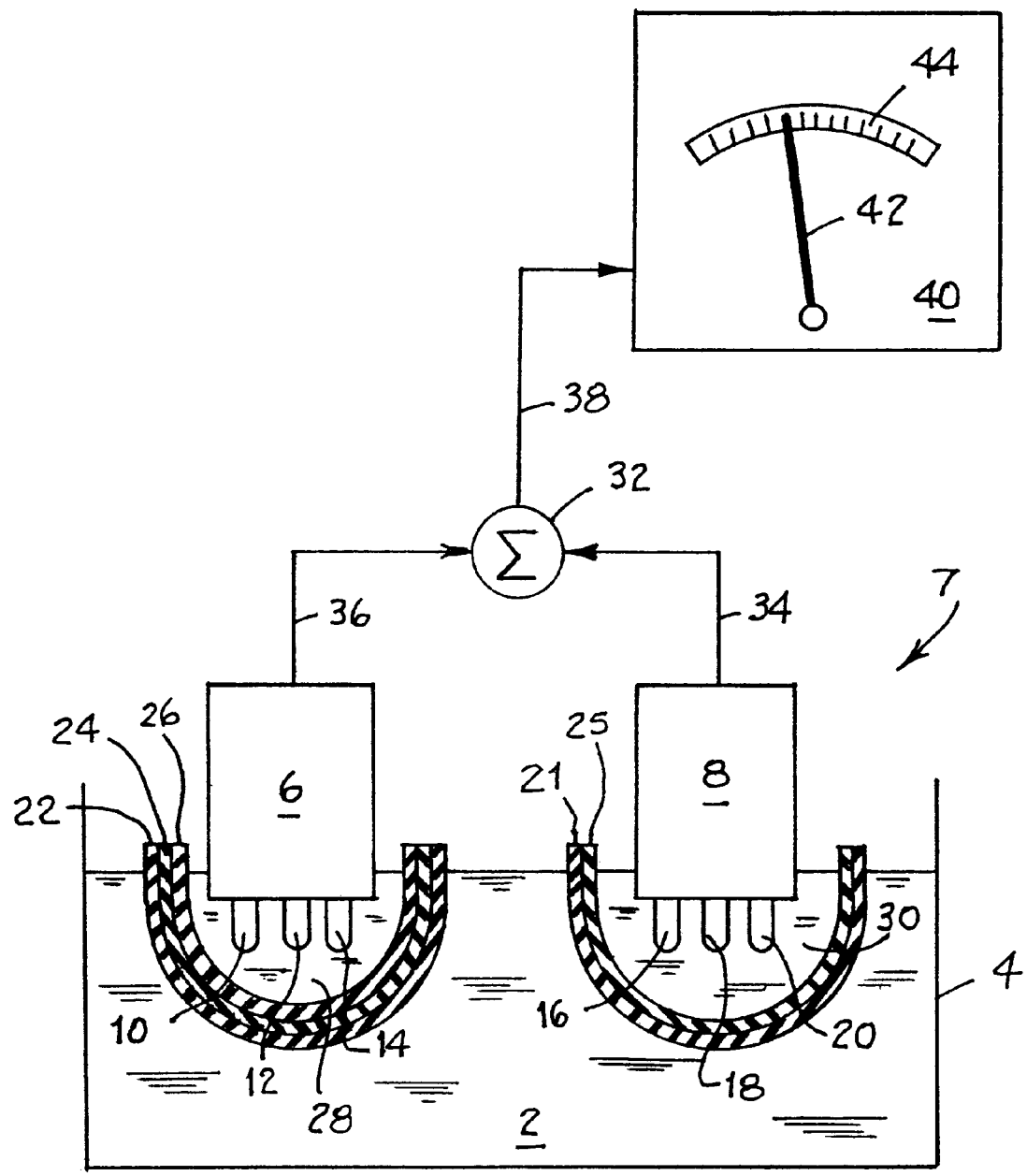
FIG. 1 is a schematic diagram of a sensor probe of the present invention disposed for testing a fluid sample for hydrogen peroxide content.

The sensor probe of this invention is best understood by reference to the drawing of FIG. 1. A sample of a hydrogen peroxide containing fluid 2 is contained in a sample vessel 4. A sensor probe 7 of this invention containing oxygen sensors 6 and 8 are positioned such that their working components are immersed below the surface of the body of fluid 2. Each sensor 6 and 8 has three electrodes which include a noble metal working electrode 10 or 16, a high impedance potential reference electrode 12 or 18, and a low impedance counter electrode 14 or 20. The working electrode 10 or 16 can be polarized at an electrochemical potential at which oxygen is electrochemically reduced. The reference electrode serves as a reference for specifying and/or fixing the potential of the working electrode to allow oxygen reduction on the working electrode. The counter electrode is the electrode to which the majority of current from the working electrode passes.

Surrounding the three electrodes of each sensor is a fluid electrolyte (electrolytic solution) respectively 28 or 30, which is chemically neutral to oxygen and which serves to permit migration of the electric charge and ionized oxygen to the appropriate electrodes. A pore-free hydrophobic membrane, respectively 25 or 26, in a cup-shaped form is disposed surrounding the three electrodes of the sensor and thus also serves as a container for the electrolyte 28 or 30. This hydrophobic membrane allows for diffusion of oxygen into the fluid electrolyte, but prevents the transport of hydrogen peroxide or electrochemical poisons or interferents and isolates the electrodes and electrolytic fluid from the fluid or fluid-containing sample or from other chemical or biological materials.

The HPGO sensor, here designated 6, is further surrounded by a cup-shaped hydrophilic membrane 24 positioned outside the hydrophobic membrane 26 (i.e., distal from the sensor 6). This hydrophilic membrane 24 contains a quantity of immobilized catalase, peroxidase or similar enzyme (preferably non-soluble) which will catalyze hydrogen peroxide according to the reaction stated above. Thus the hydrogen peroxide which disperses into the hydrophilic membrane 24 does not reach the electrolyte 28, but rather is converted to oxygen and water within the membrane 24, yielding oxygen which then diffuses on through the hydrophobic membrane 26 and into the electrolyte 28. The oxygen content of the electrolyte 28 is therefore increased respective to the oxygen content of the electrolyte 30 which surrounds the electrodes of sensor 8, with the difference in concentration being the amount of oxygen which is formed by the enzymatic reaction of the hydrogen peroxide within the membrane 24.

Each of the sensors 6 and 8 then operates to measure the oxygen content of their respective fluid electrolytes 28 and 30. Sensor 6 generates a stronger signal because the electrolyte 28 contains not only the free (background) oxygen from the sample which has diffused through the membranes 24 and 26 but also the oxygen which has been produced by the enzymatic reaction between the catalase and hydrogen peroxide in the membrane 24, whereas the electrolyte 30 contains only the background sample oxygen.

The respective oxygen-dependent signals from sensors 6 and 8 are sent through lines 34 and 36 to summer 32 where the equal background oxygen signals are cancelled, producing a resultant difference signal which is sent through line 38 to indicator 40. (The background signals cancelled also may contain a minor component from other species which are present either in the sample and diffuse into the fluid electrolytes, and which react at the sensor electrodes. Since these are normally equal at both sensors, their signal contribution is cancelled at the summer 32.) The difference signal is therefore a function solely of the content of the enzymatically produced oxygen in electrolytic fluid 28. In FIG. 1 the indicator 40 is illustrated as a simple gauge in which the position of the needle 42 relative to the scale 44 indicates the amount of the hydrogen peroxide present in the tested fluid or tissue sample. It will be recognized that at each sensor oxygen content of the fluid electrolyte is measured, and not the hydrogen peroxide content of the sample directly. However, since the oxygen content of the sample itself is identical for both sensors, and since the catalase-catalyzed reaction of hydrogen peroxide to oxygen is stoichiometric, the differential oxygen value obtained by summing of the signals provides a resultant signal which is directly proportional to the hydrogen peroxide content of the sample itself. Thus the differential oxygen value determined from the sensor signals can be read out on indicator 40 or digitally directly as hydrogen peroxide content of the fluid or meter by appropriate selection of scale dimensions and range. As indicated above, the indicator 40 could also be a form of digital readout or electronic receiver which converts the signal strength into digital format for storage, manipulation or recovery through a conventional computer system.

The hydrophobic membrane 25 or 26 will be a pore-free membrane preferably made of a material such as polydimethylsiloxane, polymers of tetafluoroethylene or its fluoro-chloro analogues or copolymers thereof with ethylene or propylene, polyethylene, polypropylene, or cellulose acetate, or a similar hydrophobic material which permits the passage of oxygen but not of hydrogen peroxide or electrochemical poisons or interferents and serves to isolate the electrolytic fluids 28 and 30 from the fluids of the sample 2.

Enzyme-containing hydrophilic membrane 24 is formed of polyacrylamine gel, glutaraldehyde cross-linked collagen or albumen, polyhydroxyethylmethacrylate, or derivatives thereof or similar hydrophilic materials. It has catalase, peroxidase, or a similar enzyme which catalyzes the conversion of hydrogen peroxide to water and oxygen dispersed throughout in a quantity sufficient to catalyze completely and thus deplete all of the hydrogen peroxide which enters the membrane 24. Since there is no enzyme-containing membrane surrounding sensor 8 and since in the absence of catalase or a similar enzyme the conversion of hydrogen peroxide to oxygen in the system is essentially nonexistent (the free oxygen and hydrogen peroxide in the sample having been in contact sufficiently long to have reached equilibrium), the concentration of oxygen present in electrolytic fluid 30 is equal to the background oxygen in the sample.

It may also be desirable to place another, "biocompatible" or "environment-compatible" membrane 21 or 22 in series outside of the membrane 24/membrane 26 pair at sensor 6 or the membrane 25 at sensor 8, to further isolate the sensors from the fluid 2 and to prevent any adverse reaction between the distal surface of the membrane 24 or 25 and the fluid 2 (or the material containing fluid 2).

The noble metal working electrode 10 or 16 will preferably be made of platinum, although other noble metals which can function to reduce oxygen may be used. The high impedance potential reference electrode 12 or 18 is preferably made of a mixture of silver and silver chloride or a similar metal or alloy which can serve as an electrical reference for specifying and/or fixing the potential of the working electrode to cause the reduction of oxygen in the sensor. The low impedance counter electrode 14 or 20 is usually made of the same material as in the working electrode, commonly platinum or another noble metal.

In many tissues from which samples of blood or other bodily fluids are drawn, there is some catalase enzyme naturally present. When analyzing such samples, it is important to test the sample with the probe of this invention as quickly as possible after the sample is drawn, before any "contaminant" catalase imported from the tissue has an opportunity to react with the hydrogen peroxide in the drawn sample and generate oxygen within the sample fluid prior to diffusion of the hydrogen peroxide and oxygen through the membranes. Since oxygen generated by the contaminant catalase will appear in the electrolyte 30 it will be indistinguishable from the true background oxygen content of the sample. Subtraction of signal of sensor 8 from the signal of sensor 6 will then produce an incorrect low signal existing from summer 32, thus causing indicator 40 to show an incorrectly low value for the amount of hydrogen peroxide present in the sample. The probe is therefore preferably constructed in a form which can be inserted directly into the tissue for the fluids to be tested in situ so that there is no time lag between hydrogen peroxide production in the tissue and detection by the sensors.

It is also important that the sensor be designed to maximize the sensitivity to hydrogen peroxide by carefully subtracting the oxygen background signal generated by both sensors, because in the most cases the background oxygen concentration is significantly higher than the hydrogen peroxide concentration, such that the resultant signal obtained by canceling the background oxygen signals is quite small compared to those background oxygen signals. A small error in determining the background oxygen signals at one or both sensors will therefore have a disproportionately large effect on the accuracy of the resultant signal so that he determination of the original hydrogen peroxide content in the fluid or tissue will be inaccurate.

Typical sensitivity of the sensor will be on the order of 0.1–0.2 $\mu$M of oxygen, and can extend into the submicromolar range. This permits measurements equivalent to those illustrated in Lacy et al, *J. Hypertens.*, 16(3):291–303 (1998); Lacy et al., *Free Rad. Biol. & Med.*, 25(6):720–727 (1998); and Swei et al., *Hypertension*, 30:1628–1633 (1997). Thus, hydrogen peroxide concentrations in the range of 1–1000 $\mu$M are expected to be detectable, with the preferred range being 1–100 $\mu$M and more preferably 10–50 $\mu$M. It will be recognized that under some carefully controlled reaction and testing conditions concentrations above or below these ranges may also be detectable.

The present sensor can be used in a laboratory, or it can be used in the field. Since all materials are present in the sensor itself (e.g., the enzyme, the membranes and the electrolyte), no additional chemicals need to be added, so the limitations imposed on prior art devices such as that described in the aforesaid PCT patent application are avoided. Similarly, since the materials remain unchanged over an extended service life of the sensor, recalibration for each usage of the sensor is not required, thus eliminating one step in operation of a hydrogen peroxide sensor and providing another significant improvement over the PCT application's device.

While the sensor of this invention has been exemplified by analysis of a blood sample, it will be recognized that it may be used in a wide variety of applications, including measuring hydrogen peroxide in physiological, environmental and industrial environments. For medical or physiological tests, the sensor may be used as a probe making direct contact with tissue or bodily fluid samples. While it is not intended as an implantable device, it can be used in combination with a catheter for continuous, intermittent or periodic analysis of, for instance, a patient's blood. In industrial or environmental settings, it may be used to detect hydrogen peroxide in the fluid or fluid-containing outflows or residues of bleaching steps in textile and paper production, in treated waste water, and numerous other reactions in which hydrogen peroxide is used as an oxidant. Those skilled in the art will recognize many other applications of the sensor of this invention.

It will be recognized that there are additional embodiments of the sensing probe which are not expressly described above, but which are clearly within the scope and spirit of the invention. The above description is therefore intended to be exemplary only, and the actual scope of the invention is to be determined solely from the appended claims.

We claim:

1. A sensing probe for quantitative determination of hydrogen peroxide present in a body of fluid or fluid-containing material, which comprises:

first and second oxygen sensors, each generating a signal proportional to oxygen content of a fluid electrolyte in contact with a respective sensor;

first and second membranes disposed in series and separating said first oxygen sensor from said material, with said second membrane being disposed between said first membrane and said first oxygen sensor;

a third membrane separating said second oxygen sensor from said material;

said first membrane being permeable to hydrogen peroxide and oxygen, and having dispersed therethrough an immobilized enzyme which catalyzes the complete conversion of hydrogen peroxide to oxygen;

said second and third membranes being hydrophobic and permeable to oxygen but not hydrogen peroxide; and a summer receiving oxygen-content-dependent signals from said first and second oxygen sensors and generating a resultant signal proportional to the difference between said oxygen-content-dependent signals, said difference being proportional to the concentration of hydrogen peroxide in said sample wherein the probe is an instant read probe.

2. A sensor probe as in claim 1 further comprising indicator means for converting said resultant signal to human- or machine-readable form.

3. A sensor probe as in claim 2 further wherein said resultant signal in human-readable form is displayed by said indicator means as a visual display from which concentration of said hydrogen peroxide in said material can be observed.

4. A sensor probe as in claim 2 further wherein said resultant signal in machine-readable form is transmitted by said indicator means to a machine capable of manipulating said machine-readable signal.

5. A sensor probe as in claim 1 wherein said first membrane is formed of a hydrophilic material having said immobilized enzyme disposed therethrough.

6. A sensor probe as in claim 5 wherein said hydrophilic material forming first membrane comprises polyacrylamine gel, glutaraldehyde cross-linked collagen or albumen, polyhydroxyethylmethacrylate, or a derivative thereof which permits the passage of molecular hydrogen peroxide and oxygen.

7. A sensor probe as in claim 1 wherein each of said second and third membranes is formed of a hydrophobic, pore-free material.

8. A sensor probe as in claim 7 wherein said hydrophobic, pore-free material forming each of said second and third membranes comprises polydimethylsiloxane, polymers of tetafluoroethylene or its fluoro-chloro analogues or copolymers thereof with ethylene or propylene, polyethylene, polypropylene, or cellulose acetate, which permits the passage of oxygen but which prevents the transport of electrochemical poisons or interferents.

9. A sensor probe as in claim 1 wherein said immobilized enzyme comprises catalase, peroxidase or an equivalent hydrogen-peroxide-catalyzing enzyme.

10. A sensor probe as in claim 1 wherein space between a proximal membrane surface and a respective one of said first and second sensor is substantially filled with said fluid electrolyte.

11. A sensor probe as in claim 1 having a sensitivity such that a concentration of hydrogen peroxide in the range of 1–1000 $\mu$M in said material can be determined.

12. A sensor probe as in claim 11 having a sensitivity such that a concentration of hydrogen peroxide in the range of 1–100 $\mu$M in said material can be determined.

13. A sensor probe as in claim 12 having a sensitivity such that a concentration of hydrogen peroxide in the range of 10–50 $\mu$M in said material can be determined.

14. A sensor probe as in claim 1 having a sensitivity such that differences in concentration of oxygen detected by said first and second sensors as low as the range of 0.1–0.2 $\mu$M can be determined.

15. A sensor probe as in claim 1 further comprising fourth and fifth membranes, said fourth and fifth membranes being biocompatible membranes and surrounding said first and second sensors, respectively.

16. A method of making a quantitative determination of hydrogen peroxide present in a body of fluid or fluid-containing material, which comprises placing said fluid or fluid-containing material in operative contact with a sensor probe as in claim 1, and operating said sensor probe to generate a human- or machine-readable indication of concentration of said hydrogen peroxide in said material.

17. A sensing probe for quantitative determination of hydrogen peroxide present in a body of fluid or fluid-containing material, which comprises:

a first oxygen sensor and a second oxygen sensor, each having electrode means for detecting the presence of oxygen in a fluid electrolyte in contact with said electrode means and for generating a signal proportional to the concentration of oxygen detected in said fluid electrolyte;

a first membrane surrounding said electrode means of said first oxygen sensor, forming a barrier between said electrode means and said material and being permeable to oxygen and hydrogen peroxide, said first membrane having disposed therethrough an immobilized enzyme which catalyzes complete conversion of hydrogen peroxide to oxygen;

a second membrane and a third membrane, said second membrane also surrounding said electrode means of said first sensor in series with said first membrane and being disposed between said first membrane and said electrode means, and said third membrane surrounding said electrode means of said second sensor and forming a barrier between said electrode means of said second sensor and said material, said second and third membranes being hydrophobic and permeable to oxygen but not hydrogen peroxide;

a summer electrically connected to said first and second oxygen sensors and receiving a signals from each sensor proportional to the amount of oxygen detected by said electrode means of said sensor, said summer comprising comparison means for determining difference in value between a signal from said first oxygen sensor and a signal from said second oxygen sensor and transmitting a difference signal proportional to said difference in value to a receiver; and said receiver comprising conversion means for receiving said difference signal and converting it into a human- or machine-readable indication of the concentration of hydrogen peroxide in said material wherein the probe is an instant read probe.

18. A sensing probe as in claim 17 wherein said electrode means of each said sensor comprises an interconnected working electrode, a reference electrode and a counter electrode.

19. A sensor probe as in claim 18 further comprising said first sensor having a first space between said electrode means and a proximal surface of said second membrane, and said second sensor having a second space between said electrode means and a proximal surface of said third membrane, each said first and second spaces having disposed therein a quantity of said fluid electrolyte, said quantity being sufficient to insure that fluid electrolyte contacts both said electrode means and a proximal membrane surface.

20. A sensor probe as in claim 17 further wherein said resultant signal in human-readable form is displayed by an indicator means as a visual display from which concentration of said hydrogen peroxide in said material can be observed.

21. A sensor probe as in claim 17 further wherein said resultant signal in machine-readable form is transmitted by an indicator means to a machine capable of manipulating said machine-readable signal.

22. A sensor probe as in claim 17 wherein said first membrane is formed of a hydrophilic material having said immobilized enzyme disposed therethrough.

23. A sensor probe as in claim 22 wherein said hydrophilic material forming first membrane comprises polyacrylamine gel, glutaraldehyde cross-linked collagen or albumen, polyhydroxyethylmethacrylate, or a derivative thereof which permits the passage of molecular hydrogen peroxide and oxygen.

24. A sensor probe as in claim 17 wherein each of said second and third membranes is formed of a hydrophobic, pore-free material.

25. A sensor probe as in claim 24 wherein said hydrophobic, pore-free material forming each of said second and third membranes comprises polydimethylsiloxane, polymers of tetafluoroethylene or its fluoro-chloro analogues or copolymers thereof with ethylene or propylene, polyethylene, polypropylene, or cellulose acetate, which permits the passage of oxygen but which prevents the transport of electrochemical poisons or interferents.

26. A sensor probe as in claim 17 wherein said immobilized enzyme comprises catalase, peroxidase or an equivalent hydrogen-peroxide-catalyzing enzyme.

27. A sensor probe as in claim 17 having a sensitivity such that a concentration of hydrogen peroxide in the range of 1–1000 $\mu$M in said material can be determined.

28. A sensor probe as in claim 27 having a sensitivity such that a concentration of hydrogen peroxide in the range of 1–100 $\mu$M in said material can be determined.

29. A sensor probe as in claim 28 having a sensitivity such that a concentration of hydrogen peroxide in the range of 10–50 $\mu$M in said material can be determined.

30. A sensor probe as in claim 17 having a sensitivity such that differences in concentration of oxygen detected by said first and second sensors as low as the range of 0.1–0.2 $\mu$M can be determined.

31. A sensor probe as in claim 17 further comprising fourth and fifth membranes, said fourth and fifth membranes being biocompatible membranes and surrounding said first and second sensors, respectively.

32. A method of making a quantitative determination of hydrogen peroxide present in a body of fluid or fluid-containing material, which comprises placing said fluid or fluid-containing material in operative contact with a sensor probe as in claim 17, and operating said sensor probe to generate said human- or machine-readable indication of concentration of said hydrogen peroxide in said material.

33. A method of making a quantitative determination of hydrogen peroxide present in a body of fluid or fluid-containing material, wherein said material comprises human or animal tissue or bodily fluid, which comprises placing said tissue or bodily fluid in operative contact with a sensor probe as in claim 17, and operating said sensor probe to generate said human- or machine-readable indication of concentration of said hydrogen peroxide in said material.

34. A method of making a quantitative determination of hydrogen peroxide present in a body of fluid or fluid-containing material, wherein said material comprises an environmental or industrial fluid or fluid-containing material, which comprises placing said environmental or industrial fluid in operative contact with a sensor probe as in claim 17, and operating said sensor probe to generate said human- or machine-readable indication of concentration of said hydrogen peroxide in said material.

* * * * *